United States Patent
Wu et al.

(10) Patent No.: US 10,467,142 B1
(45) Date of Patent: Nov. 5, 2019

(54) ENHANCEMENT OF REAL-TIME RESPONSE TO REQUEST FOR DETACHED DATA ANALYTICS

(71) Applicant: 12 Sigma Technologies, San Diego, CA (US)

(72) Inventors: Yuanpeng Wu, San Diego, CA (US); Nariaki Yamada, San Diego, CA (US); Ke Qi, Sunnyvale, CA (US); Yunqiang Chen, San Diego, CA (US); Dashan Gao, San Diego, CA (US); Xin Zhong, San Diego, CA (US)

(73) Assignee: 12 Sigma Technologies, San Diego, CA (US)

( * ) Notice: Subject to any disclaimer, the term of this patent is extended or adjusted under 35 U.S.C. 154(b) by 0 days.

(21) Appl. No.: 16/405,629

(22) Filed: May 7, 2019

(51) Int. Cl.
| | |
|---|---|
| *G06F 12/0862* | (2016.01) |
| *G06T 7/00* | (2017.01) |
| *G06T 7/11* | (2017.01) |
| *G06K 9/62* | (2006.01) |
| *G06T 1/60* | (2006.01) |

(Continued)

(52) U.S. Cl.
CPC ..... *G06F 12/0862* (2013.01); *G06K 9/00973* (2013.01); *G06K 9/6253* (2013.01); *G06N 3/08* (2013.01); *G06T 1/60* (2013.01); *G06T 7/0012* (2013.01); *G06T 7/11* (2017.01); *G06F 3/04842* (2013.01); *G06F 2212/1021* (2013.01); *G06F 2212/1024* (2013.01); *G06F 2212/6026* (2013.01); *G06K 2209/051* (2013.01); *G06K 2209/053* (2013.01); *G06T 2200/24* (2013.01); *G06T 2207/20024* (2013.01); *G06T 2207/20084* (2013.01); *G06T 2207/20092* (2013.01)

(58) Field of Classification Search
CPC ............ G06F 12/0893; G06F 12/0895; G06F 12/0897; G06F 12/0862; G06F 9/50; G06F 9/38; G06T 7/11; G06T 7/0012; G06T 1/60; G06T 1/20; G06T 1/0014; G06K 9/00973; G06K 9/6253; G06N 3/08; H04N 1/00204; H04N 1/00217
See application file for complete search history.

(56) References Cited

U.S. PATENT DOCUMENTS

| | | | | |
|---|---|---|---|---|
| 8,203,733 | B2 * | 6/2012 | Isaka | ......................... G06T 1/20 358/1.15 |
| 8,423,720 | B2 * | 4/2013 | Doring | ................ G06F 12/0862 710/305 |

(Continued)

*Primary Examiner* — Michael S Osinski
(74) *Attorney, Agent, or Firm* — Brinks Gilson & Lione

(57) ABSTRACT

This disclosure is directed to a system and a method for providing enhanced real-time or near-real-time response to request for detached data analytics services. In one implementation, a system is disclosed for predicting a data analytics service that may be requested by a user based on real-time user interactive operations, and for pre-loading/pre-configuring a pipeline of data analytics components for performing the predicted data analytics service before an actual request is made. Additionally, at least some intermediate data may be calculated by the pre-configured pipeline and may be pre-cached in memory. Upon actual user request for the data analytics service, only data analytics that require additional input data concurrently provided with the request would need to be performed. In such a manner, user-perceived delay in completing the detached data analytics service is reduced.

20 Claims, 9 Drawing Sheets

(51) Int. Cl.
  *G06K 9/00* (2006.01)
  *G06N 3/08* (2006.01)
  *G06F 3/0484* (2013.01)

(56) References Cited

U.S. PATENT DOCUMENTS

| | | | |
|---|---|---|---|
| 10,048,911 B2* | 8/2018 | Komano | G06K 15/1857 |
| 2004/0027609 A1* | 2/2004 | Isaka | B41B 27/00 |
| | | | 358/1.15 |
| 2006/0165109 A1* | 7/2006 | Kitamura | H04L 49/90 |
| | | | 370/412 |
| 2006/0274971 A1* | 12/2006 | Kumazawa | G06K 9/00993 |
| | | | 382/276 |
| 2007/0248288 A1* | 10/2007 | Nagao | G06T 1/20 |
| | | | 382/303 |
| 2008/0013862 A1* | 1/2008 | Isaka | G06T 1/20 |
| | | | 382/303 |
| 2008/0282040 A1* | 11/2008 | Doring | G06F 12/0862 |
| | | | 711/141 |
| 2009/0228677 A1* | 9/2009 | Liege | G06F 8/445 |
| | | | 711/202 |
| 2010/0094653 A1* | 4/2010 | Tribble | G06F 19/326 |
| | | | 705/3 |
| 2010/0110213 A1* | 5/2010 | Kimura | G06T 1/60 |
| | | | 348/222.1 |
| 2010/0217904 A1* | 8/2010 | Sakamoto | G06F 15/8015 |
| | | | 710/117 |
| 2011/0161629 A1* | 6/2011 | Okawara | G06F 9/3836 |
| | | | 712/200 |
| 2012/0159503 A1* | 6/2012 | Shafiee | G06F 9/5038 |
| | | | 718/104 |
| 2016/0234429 A1* | 8/2016 | Cho | H04N 5/2624 |
| 2017/0085857 A1* | 3/2017 | Feng | G06T 7/70 |
| 2017/0230526 A1* | 8/2017 | Hayashi | H04N 1/00949 |
| 2017/0255486 A1* | 9/2017 | Zhang | H04N 1/00973 |
| 2017/0318119 A1* | 11/2017 | Zbiljic | H04L 67/1097 |
| 2017/0324973 A1* | 11/2017 | Tanner | H04N 19/176 |
| 2017/0353576 A1* | 12/2017 | Guim Bernat | G06F 12/0862 |
| 2018/0005061 A1* | 1/2018 | Chang | G06T 1/20 |
| 2018/0068413 A1* | 3/2018 | Nakazono | G06F 13/1673 |
| 2018/0213104 A1* | 7/2018 | Hayashi | H04N 1/00949 |
| 2018/0307429 A1* | 10/2018 | Fu | G06F 12/0897 |
| 2018/0314941 A1* | 11/2018 | Lie | G06N 3/063 |
| 2019/0005603 A1* | 1/2019 | Chen | G06T 1/20 |

\* cited by examiner

ENHANCEMENT OF REAL-TIME RESPONSE TO REQUEST FOR DETACHED DATA ANALYTICS

TECHNICAL FIELD

This disclosure relates to a system and a method for providing real-time or near-real-time response to requests for detached data analytics services.

BACKGROUND

Data processing may be performed using complex data analytics techniques. For example, a large amount of input data may be processed by a pipeline of artificial intelligence (AI) models including but not limited to convolutional neural networks to generate outputs that contain hidden correlations and features in the input data. A platform for performing such data analytics may be hosted in backend computer servers and detached from a front-end user interface running on a remote user terminal device, and the corresponding AI models may be instantiated in the backend computer servers to form a data analytics pipeline when such data analytics service is requested from the remote terminal. Upon receiving a request for data analytics, the backend servers may need a significant amount of time to configure the data analytics pipeline, to load the AI models and target data, and to calculate intermediate data items and final output. In many applications, a real-time or near-real time response to a request for detached data analytics service may be desired and extended data processing delays may be unacceptable.

SUMMARY

This disclosure is directed to a system and a method for providing enhanced real-time or near-real-time response to requests for detached data analytics services. For example, a system and a method are disclosed for automatically and intelligently predicting a data analytics service that may be requested by a user based on real-time user interactive operations, and for pre-loading/pre-configuring a pipeline of data analytics components to perform the data analytics service before an actual request is made by the user. Additionally, at least some intermediate data may be calculated by the pre-configured pipeline and may be cached in memory for speedy access prior to the actual user request. Upon actual user request for the data analytics service, the data analytics service would have loaded and preconfigured the data analytics pipeline, calculated and cached intermediate data, and would only need to complete a portion of the data analytics that require additional input data that are provided in real-time with the request. In such a manner, user-perceived delay in completing the detached data analytics service after the service request is made may be greatly reduced.

In one implementation, a system for providing data analytics services is disclosed. The system may include a cache memory for storing preprocessed intermediate data instances and a circuitry in communication with the cache memory. The circuitry may be configured to monitor user interactive operations on a first remote terminal; automatically predict, based on the interactive operations, a data analytics service that the first remote terminal is likely to request next among a predetermined plurality of data analytics services. Prior to receiving a request from the first remote terminal for the data analytics service, the circuitry is further configured to, automatically, identify a target data item for the data analytics service based on the interactive operations, determine a pipeline of data analytics models associated with the data analytics service and corresponding model parameters, instantiate the pipeline of data analytics models from a model repository and pre-configure the data analytics models with the corresponding model parameters, and pre-process the target data item using a first portion of the instantiated and pre-configured pipeline of data analytics models into an intermediate data instance and store the intermediate data instance in the cache memory. Upon receiving from the first remote terminal the request to perform the data analytics service, the circuitry is further configured to process the cached intermediate data instance by a second portion of the instantiated and pre-configured pipeline of data analytics models according to at least one additional processing parameter in the request to perform the data analytics service.

In the implementation of the system above, the circuitry may be further configured to determine whether to remove the intermediate data instance from the cache memory after completion of the requested data analytics service based on monitoring additional user interactive operations from the first remote terminal.

In any of the implementations of the system above, the circuitry may be configured to remove the intermediate data instance from the cache memory after completion of the requested data analytics service and after determining that the additional user interactive operations from the first remote terminal indicate that a user of the first remote terminal has stopped operating on the target data item for a predetermined period of time.

In any of the implementations of the system above, the circuitry may be further configured to monitor interactive operations and requests for data analytics services from at least one second remote terminal; and the cache memory may be further configured to store a data instance map for associating each of the pre-processed intermediate data instances with one or more remote terminals among the first remote terminal and the at least one second remote terminal.

In any of the implementations of the system above, the circuitry may be further configured to determine whether to remove an association between the intermediate data instance generated by the first portion of the pipeline of data analytics models and the first remote terminal from the data instance map after completion of the requested data analytics service, based on monitoring additional user interactive operations from the first remote terminal.

In any of the implementations of the system above, the circuitry may be further configured to identify an inactive intermediate data instance and remove the inactive intermediate data instance from the cache memory.

In any of the implementations of the system above, the circuitry may be configured to identify the inactive intermediate data instance by determining that a corresponding intermediate data instance has no association with any of the first remote terminal and the at least one second remote terminal.

In any of the implementations of the system above, the target data item may include a medical image; and the target data item is displayed in an interactive user interface of the first remote terminal.

In any of the implementations of the system above, the circuitry may be configured to automatically predict the data analytics service by performing predictive analytics of user interactive operations on the target data item displayed on the interactive user interface of the first remote terminal using deterministic or stochastic models based on the user's workflow.

In any of the implementations of the system above, the data analytics service may include a nodule detection service for identifying a nodule in the medical image, and the pipeline of data analytics models may include an image segmentation model for generating a mask for a predetermined organ in the medical image and a nodule segmentation model for identifying a nodule in the medical image.

In any of the implementations of the system above, the image segmentation model and the nodule segmentation model each may include a plurality of convolutional neural network layers, the first portion of the instantiated and pre-configured pipeline of data analytics models may include the image segmentation model, the second portion of the pipeline of data analytics models may include the nodule segmentation model. The intermediate data instance generated by the first portion of the pipeline of data analytics models may include the medical image filtered by the mask for the predetermined organ.

In any of the implementations of the system above, the additional processing parameter in the request to perform the data analytics service from the first remote terminal may include a user-selected location in the image displayed on the interactive user interface of the first remote terminal as indicated by a cursor click operation by a user initiating the request. The circuitry is configured to process the cached intermediate data instance by the nodule segmentation model according to the user-selected location to determine a mask for a nodule in a vicinity of the user selected location in the medical image.

In any of the implementations of the system above, the pipeline of data analytics models further may include a data normalization model for normalizing the medical image filtered by the mask. The first portion of the pipeline of data analytics models may include the image segmentation model and the data normalization model. The second portion of the pipeline of data analytics models may include the nodule segmentation model. The intermediate data instance may include the medical image filtered by the mask and filtered by the data normalization model.

In any of the implementations of the system above, the pipeline of data analytics models further may include a malignancy detection model for predicting whether the nodule identified by the nodule segmentation model is malignant.

A method is further disclosed for providing data analytics services by a system circuitry. The method includes monitoring user interactive operations on a first remote terminal; and automatically predicting, based on the interactive operations, a data analytics service that the first remote terminal is likely to request next among a predetermined plurality of data analytics services. The method further includes, prior to receiving a request from the first remote terminal for the data analytics service, automatically, identifying a target data item for the data analytics service based on the interactive operations, determining a pipeline of data analytics models associated with the data analytics service and corresponding model parameters, instantiating the pipeline of data analytics models from a model repository and preconfigure the data analytics models with the corresponding model parameters, and pre-processing the target data item using a first portion of the instantiated and pre-configured pipeline of data analytics models into an intermediate data instance and storing the intermediate data instance in a cache memory. The method further includes, upon receiving from the first remote terminal the request to perform the data analytics service, processing the cached intermediate data instance by a second portion of the instantiated and pre-configured pipeline of data analytics models according to at least one additional processing parameter in the request to perform the data analytics service.

In the implementation of the method above, the method may further include removing the intermediate data instance from the cache memory after completion of the requested data analytics service and after determining that additional user interactive operations from the first remote terminal indicate that a user of the first remote terminal has stopped operating on the target data item for a predetermined period of time.

In any of the implementation of the method above, the target data item may include a medical image. The target data item may be displayed in an interactive user interface of the first remote terminal. The data analytics service may include a nodule detection service for identifying a nodule in the medical image. The first portion of the pipeline of data analytics models may include an image segmentation model for generating a mask for a predetermined organ in the medical image. The second portion of the pipeline of data analytics models may include a nodule segmentation model for identifying a nodule in the medical image. The intermediate data instance processed by the first portion of the pipeline of data analytics models may include the medical image filtered by the mask for the predetermined organ.

DETAILED DESCRIPTION

Figure 1:
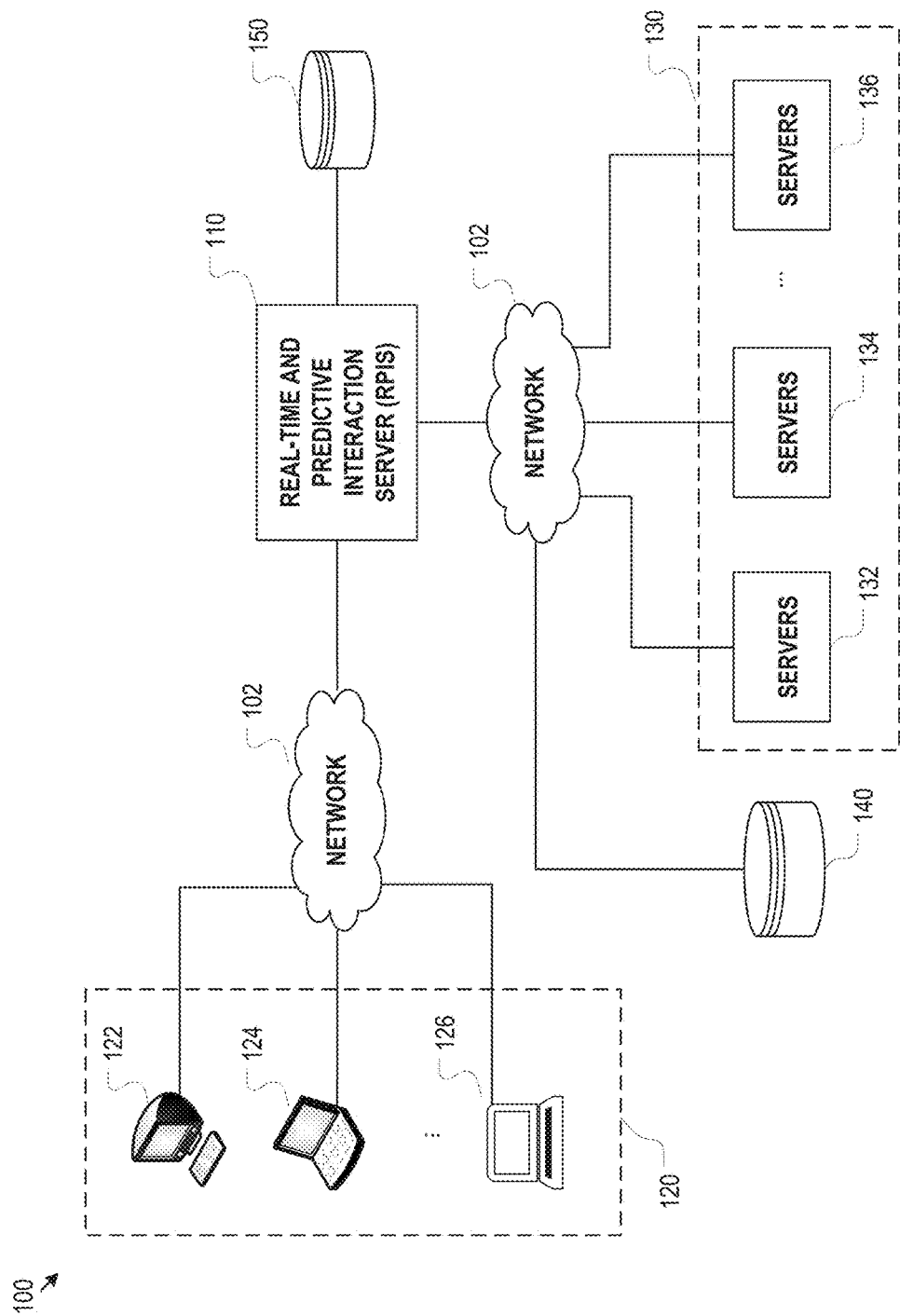
FIG. 1 illustrates an example system for providing real-time response to requests for detached data analytics services.

Even with the emergence of powerful modern computer servers, analytics of a large collection of input data may still take a great amount of time to complete, making real-time or near-real-time (these two terms are used interchangeably)

on-demand provisioning of a data analytics service difficult to achieve. In providing such a data analytics service in response to a remote service request, the servers may need to (1) obtain a target dataset, often via a communication network from a remote location, (2) load the target dataset into memory, (3) load and configure a data analytics pipeline according to the requested data analytics service, and (4) process the target dataset through the data analytics pipeline to generate output data items, and (5) present the output data items to the remote requester of the data analytics service.

Each of these steps may take a significant amount of time to perform due to the complexity of the data analytics pipeline and the size of the data flowing through the data analytics pipeline. For example, the target dataset may be large and may include tens to hundreds of megabytes, multiple gigabytes, or terabytes of information at a time. As such, loading the target dataset either entirely or partially into a memory space for processing may be very time consuming. For another example, the data analytics pipeline may be extremely complex, and may include various distinct but linking data analytics engines each separately provisioned and hosted centrally or distributed geographically in distinct locations. Each of these data analytics engines may further include a collection of data analytics components for processing the target dataset, for generating intermediate data items, and for further processing these intermediate data items. These data analytics components may include but are not limited to artificial intelligence (AI) models that are particularly suitable for automatically combing through a large amount of input data to identify hidden features and hidden correlations that are otherwise difficult to extract, and for automatically transforming the input target dataset or the intermediate data items into representations of alternative forms or domains. Loading, configuration, and running of these complex data analytics models may also be very time-consuming.

Each of these AI models may be pre-trained to handle a particular pre-defined intelligent data analytics task including but not limited to categorization, classification, segmentation, clustering, and pattern recognition of the input data. For example, such an AI model may include a deep learning convolutional neural network (CNN) having multiple cascading convolutional, pooling, rectifying, and/or fully connected layers of neurons, with millions of kernel, weight, and bias parameters. These parameters may be determined by training the CNN using a sufficient collection of input data labeled with ground-truth categories, boundary boxes, segmentation masks, and any other types of features pertinent to the particular task being handled by the CNN. In an exemplary training process of a CNN model, each of a large number of labeled training datasets may be forward propagated through the layers of neurons of the CNN network with predetermined inter-connectivity and training parameters to calculate an end labeling loss or error. Back propagation may then be performed in an opposite direction through the layers of the interconnecting neurons while adjusting the training parameters to reduce labeling loss based on gradient descent. The forward and back propagation training process for all training datasets iterates until the neural network produces a set of training parameters that provide converging minimal overall loss for the labels predicted by the neural network over the ground truth labels pre-associated with the training datasets. A converged model may then include a final set of training parameters and neural connectivity, and may then be stored in an AI model repository. Such a CNN model typically must be of sufficient size in terms of the number of neural network layers and number of neurons/features in each neural network layer for achieving acceptable predictive accuracy. The number of training parameters is directly correlated with the size of the neural network, and is typically extraordinarily large even for a simple AI model (on the order of millions, tens of millions, hundreds of millions, and thousands of millions of parameters).

In a platform for on-demand data analytics services, a service request may be made with the target dataset specified or identified. In response to the service request, backend servers may begin fetching the target dataset, and configuring an appropriate data analytics pipeline for processing the target dataset. Due to the reasons described above, the requester of the data analytics services may have to wait until the target dataset is processed and the requested data analytics service is completed before the outcome of the data analytics service is available for presentation to the requester.

In the various exemplary implementations described in this disclosure, a pre-configuration of the data analytics pipeline and some amount of pre-processing are performed prior to an actual request for service. As such, a perceived response time to request for detached data analytics services is reduced. In order to prepare the correct data items and pre-configure the correct data analytics pipeline, these implementations are also capable of predicting a data analytics service that the requester is likely to make among a predetermined plurality of data analytics services before an actual service request is made by the user. The time lapse between the prediction of the data analytics service to be requested and the actual request may then be utilized for data preparation and for pre-configuration of the predicted data analytics pipeline. In some implementations, the pre-configuration and pre-processing of the predicted data analytics pipeline may be performed prior to receiving the actual request for the data analytics service to the extent that the only tasks left to perform after receiving the actual request are those requiring processing parameters that can only become available when the actual request for the data analytics service is made. Those remaining tasks may take much less time to complete following the receipt of the actual request for the data analytics service. The requester thus may experience little time lag in receiving the outcome of the requested data analytics service after making the request. In other words, the requester may experience real-time or near real-time response to requests for data analytics services.

An example system for providing real-time or near-real-time response to requests for data analytics services is illustrated in 100 of FIG. 1. As shown in FIG. 1, system 100 may include backend servers 132, 134, and 136 for hosting various data analytics services. System 100 may further include remote terminals 122, 124, and 126 for users to access the various data analytics services via a real-time and predictive interaction server (RPIS) 110. The various servers and remote terminals are connected via public or private communication networks 102. As will be shown in more detail below, the RPIS 110 performs prediction of data analytics service, provisioning of pre-configuration of the predicted data analytics service, and pre-processing of data associated with the predicted data analytics service. System 100 further includes repositories 140 and 150 for data and for various data analytics models.

Figure 2:
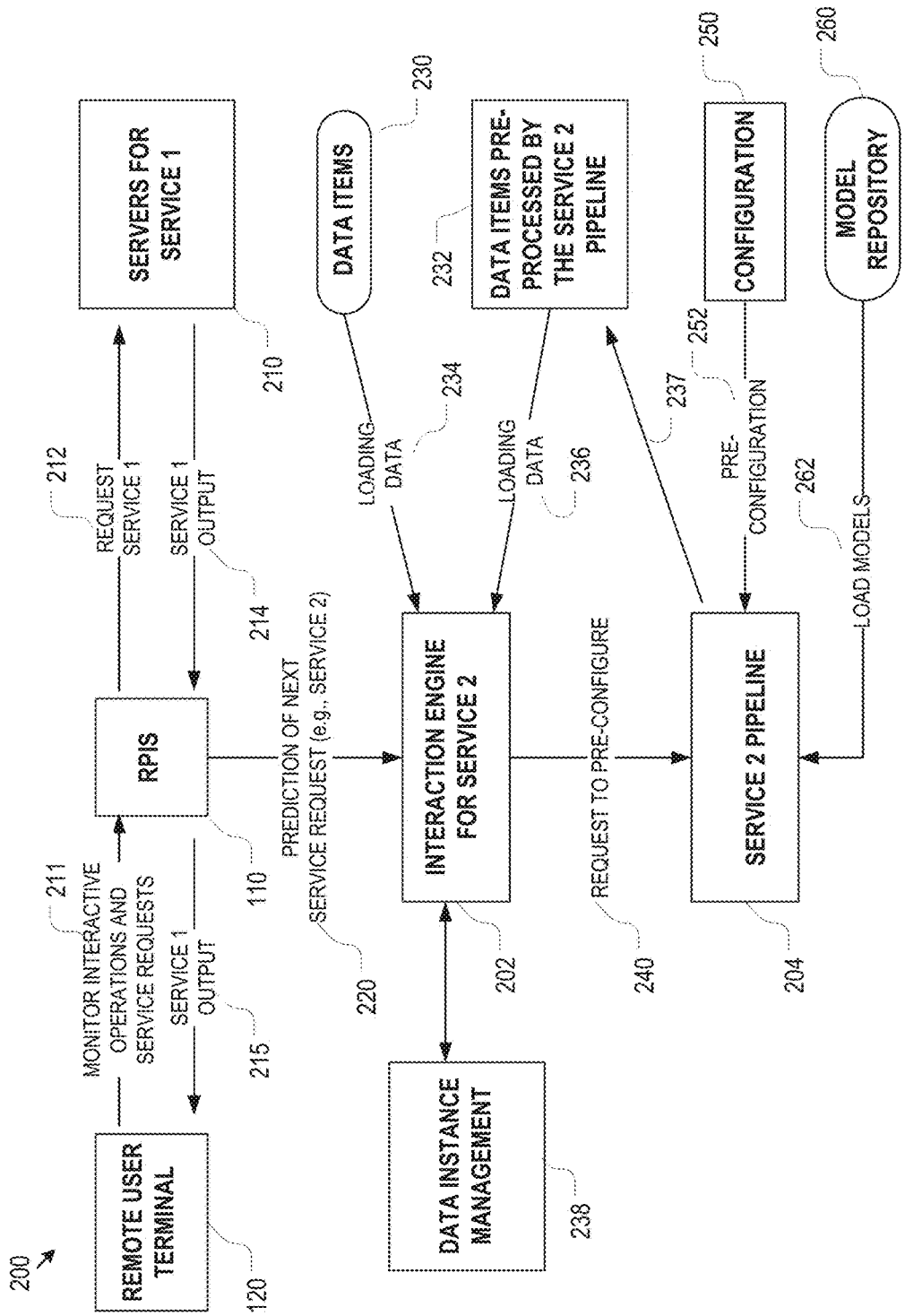
FIG. 2 illustrates example components of a system for providing real-time response to requests for detached data analytics services.

FIG. 2 shows an example system 200 that illustrates the role of the RPIS 110 of FIG. 1. The RPIS 110, for example, may be responsible for monitoring various activities at the remote user terminal 120 in real-time, as shown by 211. User activities at the remote user terminal 120 as monitored by the RPIS 110 may include but are not limited to user commands and other user interactive operations detected at a user interface running at and displayed on the user terminal, User commands, for example, may include user requests for data analytics services. User interactive operations may include a broad range of user operations and manipulations in the user interface displayed on the user terminal. Such interactive operations, for example, may include cursor movements, curser clicks/activations, keystrokes, data selections, and folder/file access. The user activities at the user terminal may be communicated to the RPIS 110 in real-time in the form of, for example, system messages or notifications. The RPIS 110 may automatically analyze these user activities to identify patterns and trends, to determine currently issued user request for data analytics services, and to predict data analytics services that the user is likely to request in the near future.

In the example shown in FIG. 2, the RPIS 110 may receive a user request for service 1 while monitoring the user activities at the user terminal 120. Service 1 may or may not be one of a plurality of data analytics services provided by system 200. Upon receiving the request for service 1, the RPIS 110 communicates with servers 210 associated with service 1, as shown by arrow 212. Upon receiving the request for service 1, the servers 210 proceed to perform configuration and setup of processing modules needed for provisioning service 1. Once the requested service 1 is rendered at the servers 210, the outcome may be returned by the servers 210 to the user terminal 120 via the RPIS 110 for presentation at the user terminal 120, as shown by arrows 214 and 215.

The RPIS 110 may further analyze the interactive operations and service requests made by the user terminal 120 in real-time, and automatically predict the next service request that the user terminal is likely to make in the near future. For example, a series of user interactive operations and prior service requests may be indicative of a likelihood that the user may request service 2 in the near future. A predictive model may be used by the RPIS for identifying the most likely next user service request. Such a predictive model may be developed based on past user behaviors and habits in using the user interface at the remote terminal. Some examples of the predictive models may include, but are not limited to, deterministic models such as a clinical workflow, and stochastic models such as finite state machines or hidden Markov models.

The RPIS 110 may communicate the real-time prediction of future request for service 2 to an interaction engine 202 associated with the provisioning of service 2 before an actual request for service 2 is issued from the remote user terminal 120, as shown by the arrow 220 of FIG. 2. The interactive engine 202 may thus begin pre-processing in anticipation of providing service 2 to the user terminal. For example, the interactive engine 202 may request data items 230 and cache/load these data items in memory for fast access if they have not yet been loaded previously (234). These data items, for example, may include but are not limited to target input dataset for the data analytics service 2. For another example, the interactive engine 202 may further initiate pre-configuration of a data analytics pipeline for service 2, as shown by 240 and 204. The pipeline for data analytics of service 2 may include a plurality of interconnecting processing components. As such, the data analytics pipeline may be pre-configured according to configuration prescription 250 for service 2, as shown by 252. One or more data analytics models may be invoked by these processing components as specified in the configuration prescription 250. These data analytics models, for example, may be based on complex AI neural networks. The pre-configuration of the data analytics pipeline for service 2 may thus further include pre-loading the various data processing components and AI models (262) from a model repository 260. Loading the AI models based on deep learning neural networks, for example, may include loading the neural network construction of the models and the various model parameters for each neuron in the neural network construction.

Once pre-configured and with the models loaded, the data analytics pipeline 204 may be ready to perform service 2 for the user terminal before an actual service request is received by the RPIS 110. Data items and/or service parameters, however, may only be partially available. For example, some data items and/or service parameters may only be specified when the actual service request is made by the user terminal 120 and RPIS 110. As such, the data analytics pipeline 204 may not be able to complete the predicted service prior to receiving the actual service request from the user terminal 120 and the RPIS 110. However, the interaction engine 202 may be configured to cause a portion of the data analytics pipeline to perform data pre-processing to the extent that relevant input data items have become available and prior to receiving the actual service request from the user terminal 120 and the RPIS 110. By proceeding with the data pre-processing, the data analytics pipeline 204 may generate intermediate data items that may be needed later when the actual service request from the user terminal 120 and the PRIS 110 is received. The data pre-processing and generation of intermediate data items are illustrated by 237 and 232 of FIG. 2, respectively. The intermediate data items may be further cached in memory as indicated by the arrow 236.

In some implementations based on FIG. 2, the data preprocessing by the data analytics pipeline 204 may be performed to the fullest extent possible. As such, the remaining data analytics tasks that are not commenced during the data pre-processing stage may be the ones that require data or parameters that will only become available when the actual request for data analytics service 2 is made. These tasks may be commenced and completed after receiving the actual service request. Because a significant amount of pre-configuration 252, model loading 262, and data pre-processing 237 have been completed prior to receiving the actual service request, the time lag between the time of service request and time of service completion may be greatly reduced, In FIG. 2, the preloaded data items 230 and intermediate data items 232 pre-processed by the data analytics pipeline 204 may be cached in memory for quick access by the processing components of the data analytics pipeline 204. These data items may be managed as in-memory data instances. A data instance map may be further maintained by the interaction engine 202, as shown by 238. These data instances may be added or removed from the memory as data analytics services are predicted, configured, and completed. As the system 200 may be further configured to support service requests from multiple user terminals having respective user identities, the data instances cached in the memory and the corresponding data instance map may be managed in a manner such that the data instances may be shared by different user terminals. Further, data instances may be shared among different data analytics services. In accordance, the data instance map may be constructed to provide association between data instances, remote terminals (user identities), and data analytics services that are actively using the data instances. More details for managing the data instances and data instance map will be described with respect to FIG. 8.

Figure 3:
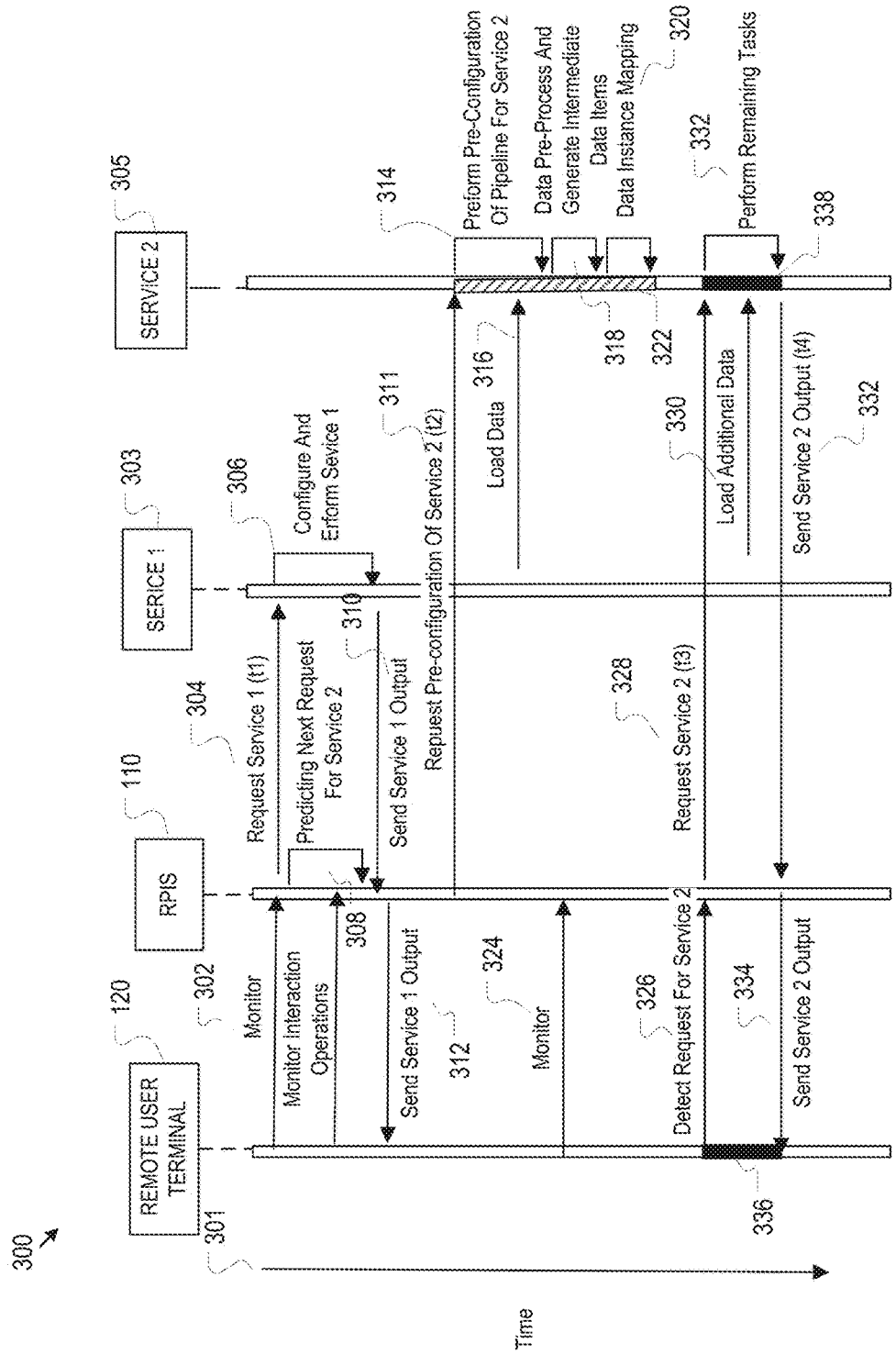
FIG. 3 illustrates an example logic flow for providing real-time response to requests for detached data analytics services.

FIG. 3 further illustrates a timeline 300 for the example implementation of providing predictive data analytics service in FIG. 2. In FIG. 3, arrow 301 shows a progression of time. In FIG. 3, the RPIS 110 is responsible for constantly monitoring the user activity in the user interface on the user terminal 120 throughout the provisioning of the data analytics services, as shown by 302 and 324. For example, while monitoring the user activity at the user terminal 120, the RPIS 11'0 detects at time t1 that a request for service 1 (303) is made by the remote user terminal 120, as shown by 302. The RPIS 110 then sends the request for service 1 at time t1 (time lag from the detection of the request is ignored for simplicity) to servers associated with service 1 (303), as shown by 304. Upon receiving the request for service 1, the servers associated with service 1 configure and perform service 1, as shown by 306. The output of service 1 may be communicated to the RPIS 110, as shown by 310, and to the requesting remote user terminal 120, as shown by 312. The RPIS 110 may further perform prediction of the next service request by analyzing the constantly monitored user activity information from the remote user terminal 120 and the prior service requests made by the user (such the request for service 1 made at time t1). For example, the RPIS 110 may predict service 2 as the next data analytics service to be requested by the remote user terminal 120. The RPIS 110 then sends a request for pre-configuration of service 2, at time t2, to servers associated with the provisioning of service 2, as illustrated by 311.

The servers associated with service 2 may begin pre-configuration of service 2 once the pre-configuration request is received, as shown by 314. During the pre-configuration process, the data analytics pipeline for service 2 and various data analytics models may be loaded. Further, existing data that may be needed for providing service 2 may be loaded, as shown by 316. In addition, a portion of the data analytics pipeline may be used to pre-process target data items to generate intermediate data items, as shown by 318 of FIG. 2. The loaded data, including the existing data items loaded in step 316 and the intermediate data items generated in step 318 may be managed as mapped in-memory data instances by the servers associated with service 2, as shown by 320. Although processes 314, 316, 318, and 320 are illustrated as being arranged in a particular sequence in FIG. 3, they may be performed in any overlapping or non-overlapping order. The shaded bar 322 illustrates an exemplary time duration for the data preparation, pre-processing, and pre-configuration of service 2 before an actual request for service 2 is received from the remote user terminal 120.

In FIG. 3, the RPIS 110 may continue to monitor the user activities at the user interface in the remote user terminal 120. At time t3, an actual request for service 2 is detected from the remote user terminal 120, as shown by 326. The RPIS 110 then sends the request to servers associated with service 2, as shown by 328. The request may include or may identify additional input data items needed for the requested service 2, and such data may be loaded by the data analytics pipeline for service 2, as shown by 330. The remaining data analytics tasks may then be performed by a second portion of the data analytics pipeline for service 2, as shown by 332. At t4, the data analytics pipeline completes the requested service 2, generates an output, and communicates the output to the RPIS 110, as shown by 332. The data analytics output is further communicated to the remote user terminal 120 for presentation, as shown by 334.

The dark bars 336 and 338 in FIG. 3 thus represent the time lapse between t3 (the time when the actual request for service 2 is made and communicated) and t4 (the time when the requested service 2 is completed). Such time lapse may be much shorter than the time duration required for performing the requested service 2 if the RPIS 110 is not capable of predicting the future request and no pre-configuration and pre-processing are performed by the data analytics pipeline for service 2.

The implementations described above may be applicable for predictive provisioning of data analytics services of any type of target dataset. These implementations may be particularly adapted for data analytics of medical images. Such medical images may include but are not limited to Computed Tomography (CT) images, Magnetic Resonance Imaging (MRI) images, ultrasound images, X-Ray images, and the like. In some implementations, data analytics may be performed on a target medical image for Computer Aided Diagnosis CAD. For example, a medical image may be analyzed to identify nodules in an organ and to classify the identified nodules (for example, as either benign or malignant). Such CAD may be used by a radiologist or doctor to facilitate their evaluation of the medical image.

Figure 4:
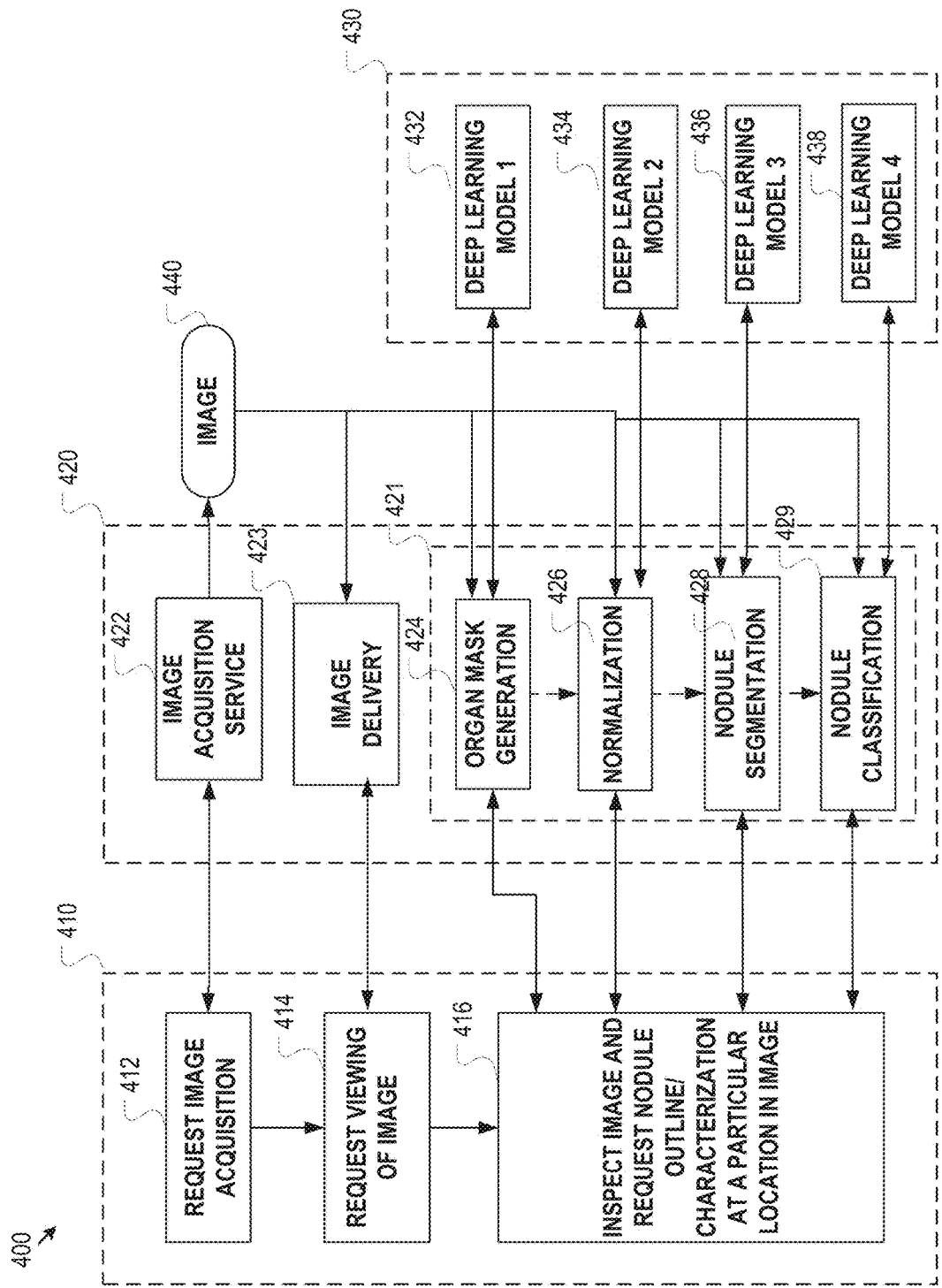
FIG. 4 illustrates a hierarchy of data analytics components in an example application for processing medical images.

In an example application shown in 400 of FIG. 4, a radiologist or doctor (herein referred to as radiologist) may use a remote terminal to request various types of data acquisition and data analytics services, as shown by 410. Examples of these data acquisition and analytics services are shown in 420 of FIG. 4. Some of the data analytical services may be provided by a data analytics pipeline 421. Each of these data analytics pipeline may invoke one or more deep learning models 430 from a repository for AI models.

For example, the radiologist may request an image acquisition for a patient, as shown by 412 of FIG. 4. The requested image acquisition service may be provided by 422. The image acquisition service may generate a medical image 440 for the patient. The acquired medical image 440 may be stored in an image repository.

As further shown by 414 of FIG. 4, the radiologist may request electronic delivery of the acquired medical image of the patient for viewing and for visual evaluation on a user interface of a remote terminal device operated by the radiologist. Such a request may be serviced by the image delivery service 423. In particular, the image delivery service may be responsible for identifying the medical image requested by the radiologist among a plurality of medical images stored in the medical image repository, and electronically deliver the requested medical image 440 to the remote terminal for the radiologist to view.

As shown by 416 of FIG. 4, the radiologist may perform visual inspection and evaluation of the requested medical image. The radiologist may perform various interactive operation at the user interface of the remote terminal while inspecting the requested medical image. The radiologist may observe a suspicious region in the medical image and may request a nodule detection service for segmenting and outlining one or more nodules in the vicinity of the suspicious region. For example, the radiologist may perform a mouse click on the image to indicate a point location of the suspicious region. Alternatively, the radiologist may draw a boundary box in the image to indicate an area location of the suspicious region. The request for nodule detection may include the point or area locations selected by the radiologist. The request for nodule detection service may then be performed by the nodule detection service pipeline 421.

As further shown in FIG. 4, the nodule detection service pipeline 421 may include multiple interconnecting data analytics components. For example, the nodule detection service pipeline 421 may include an organ mask generation component 424, an image normalization component 426, and a nodule segmentation component 428, and a nodule classification component 429. Each of these components may require input data such as the medical image 440 and/or intermediate data from a preceding stage of the pipeline. For example, the organ mask generation component 424 may process the input medical image 440 to generate a mask for a particular organ of interest. Such a mask may be used to filter the image data 440 to retain only image data that are within the organ. The data normalization component 428 may analyze the filtered image data from the organ mask generation component 424 to generate a normalized image data. The normalization process, for example, may convert the image data into standard view perspectives and standard intensity ranges. The nodule segmentation component 428, for example, may further process the filtered and normalized image data to identify nodules and their boundary boxes or outlines in the vicinity indicated by in the request from the radiologist. The nodule classification component 429 may be used to analyze the segmented nodule image data to determine the characteristics of the nodules. For example, it may determine whether each of the segmented nodules is benign or malignant.

Some of the data analytics components of the nodule detection service pipeline 421 may be based on one or more AI models 432, 434, 436, and 438. Each of these models may include a pre-trained multilayer CNN. For example, the organ mask generation component 424 and nodule segmentation component 428 may be based on separately and independently trained deep learning CNN models for image segmentation. The nodule classification component 429, for another example, may be based on a pre-trained deep learning CNN classifier.

Examples for the deep learning models to processing digital medical images have been disclosed in patent applications belonging to the same Applicant as this current application, including but not limited to U.S. patent application Ser. No. 15/943,392, filed with U.S. Patent Office on Apr. 2, 2018, U.S. patent application Ser. No. 16/104,449, filed with U.S. Patent Office on Aug. 17, 2018, PCT International Patent Application No. PCT/US2018/57529, filed with the U.S. Patent Office on Oct. 25, 2018, and PCT International Application No. PCT/US2017/035052, filed with the U.S. Patent Office on May 30, 2017, the entirety of which are herein incorporated by reference.

The predictive pre-configuration of data analytics implementations described in FIGS. 1-3 may be applied to the medical image processing and CAD application setting of FIG. 4. For example, before an actual request for the nodule detection service is made by the radiologist from the remote terminal, the RPIS of FIGS. 1-3 may be employed for monitoring the interactive operations of the radiologist for predicting the next data analytics service that the radiologist is likely to request in the near future. For example, based on the interactive operation by the radiologist on the medical image displayed on the remote terminal, the RPIS may predict that the radiologist may be interested in the a nodule detection service, even though the particular location around which the radiologist would like to have nodules detected is not yet known. With such prediction, the RPIS 110 may then arrange for a pre-configuration of the nodule detection pipeline 421, load the deep learning models 430, cache the image 440 prior to any actual request for nodule detection service. The RPIS may further configure a portion of the pipeline 421 to perform pre-processing of data prior to any actual request for the nodule detection service if the input data for such a portion are already available. For example, because the target image data 440 may have already been predicted and identified prior to the actual request for nodule detection services, the organ mask generation portion 424 and the data normalization portion 426 of the nodule detection pipeline 421 may be preprocessed. When the radiologist eventually makes a request for nodule detection service by clicking a particular suspicious area in the image, the image data would have already been filtered by the preprocessed organ mask and been normalized. The nodule detection pipeline 421 would then only need to complete the nodule segmentation portion 428 and nodule classification portion 429. In some implementations, some sub-tasks within the nodule segmentation portion 428 and the nodule classification portion 429 may be independent of the radiologist-specified location. Those sub-tasks may also be pre-processed prior to the actual request for nodule detection service.

Figure 5:
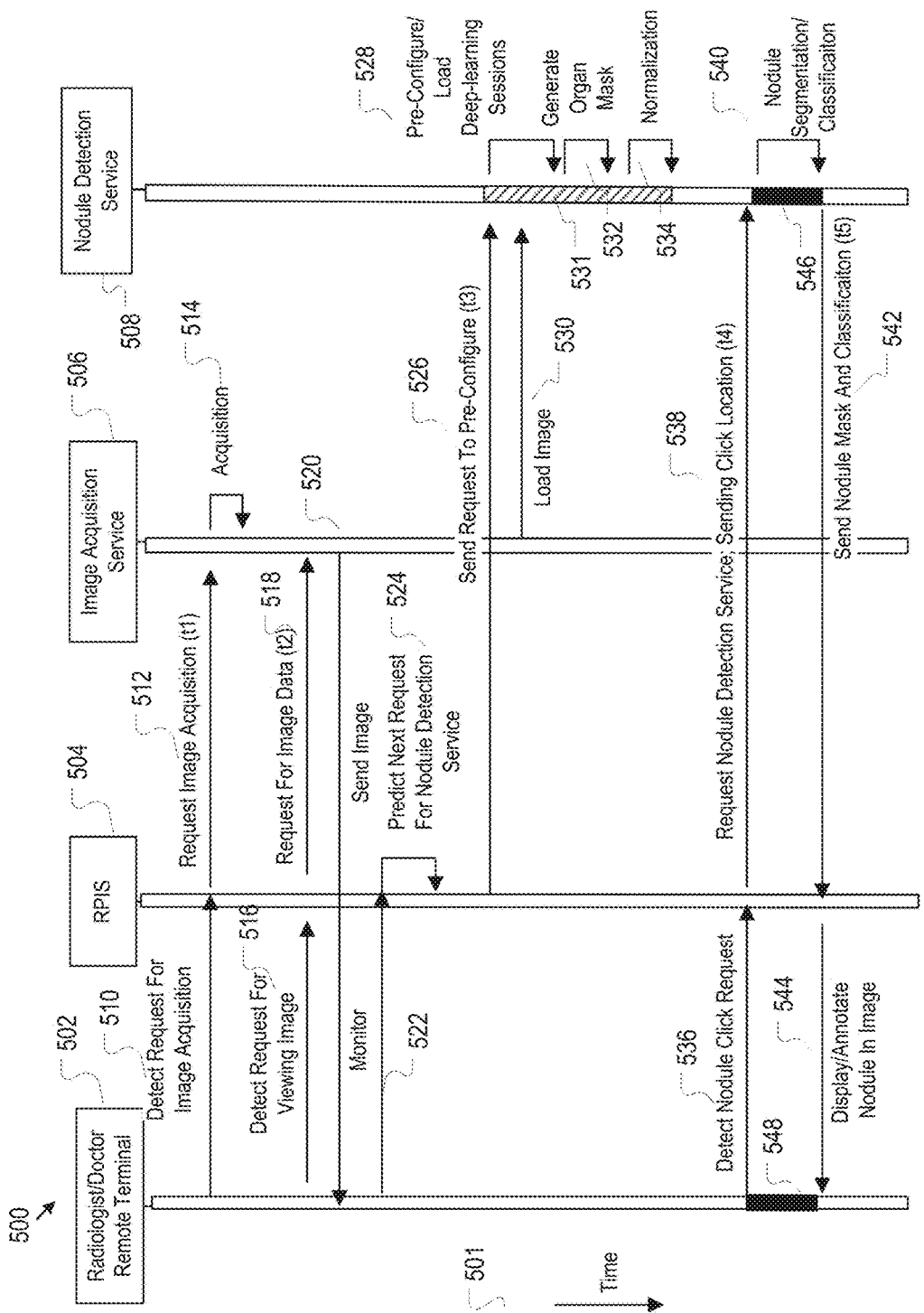
FIG. 5 illustrates an example logic flow for providing real-time response to requests for processing medical images.

FIG. 5 shows an example time line for such a predictive pro-processing of data analytics service in the medical image processing and CAD application. The time axis is indicated by 501. At time t1, the radiologist may make a request for image acquisition for a patient (510) from terminal 502 and such a request may be detected by the RPIS 504. The request is then sent to the image acquisition service 506. The image acquisition service acquires the medical image for the patient (514) and stores the image in a medical image repository. At time t2, the RPIS 504 detects a request for viewing/inspecting the medical image of the patient from the radiologist terminal 502. The RPIS 504 sent the request to the image acquisition service (or a separate image delivery service) (518) and the medical image is returned to the radiologist terminal for viewing (520).

The RPIS may continue to monitor the interactive operation by the radiologist, (522) and may predict, based on the interactive operations of the radiologist, that the next service request is likely to be a nodule detection service (524). The RPIS 504 then send a request for pre-configuration to the nodule detection service 508 at t3 (526), when the request for nodule detection service is predicted. The nodule detection service then proceed to pre-configure the nodule detection pipeline and load the deep-learning models (528), and load target dataset (such as the medical image for the patient) (530). The nodule detection service 508 further runs a portion of the nodule detection pipeline for data preprocessing, such as organ masking (532) and data normalization (534), all before an actual request for nodule detection service is made by the radiologist from the terminal 502.

At time t4, the actual request for nodule detection service is detected (536) and the request is sent by the RPIS 504 to the nodule detection service 508 (538). The nodule detection service then proceeds to run the portion of the nodule detection pipeline that generate nodule segmentation masks and that classifies the detected nodules (540), The nodule masks and classification may be generated at time t5 and may be sent to the terminal 502 for display to the radiologist (544).

In the implementation of FIG. 5, the pre-configuration and the nodule detection pipeline and pre-processing by a portion of the pipeline may be predictively performed during the time period indicated by the shaded bar 531, prior to the actual request for nodule detection service. The time lapse between the time when the request for nodule detection service is made and when the nodules are segmented and classified is indicated by the dark bar 546 (or 548) and is greatly reduced due to the predictive pre-configuration and data pre-processing described above.

Figure 6:
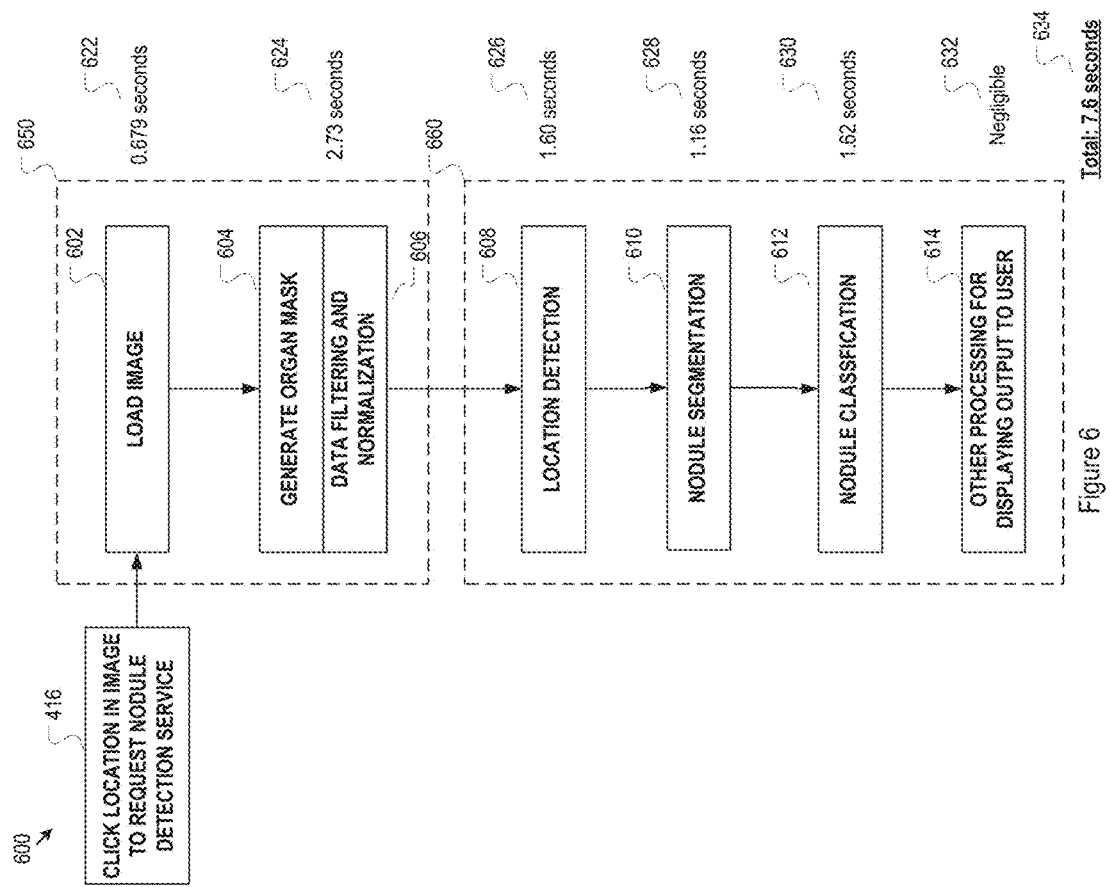
FIG. 6 illustrates an example response time to a request for identifying and analyzing nodules in a medical image using a data analytics pipeline without predictive pre-configuration and pre-processing.
Figure 7:
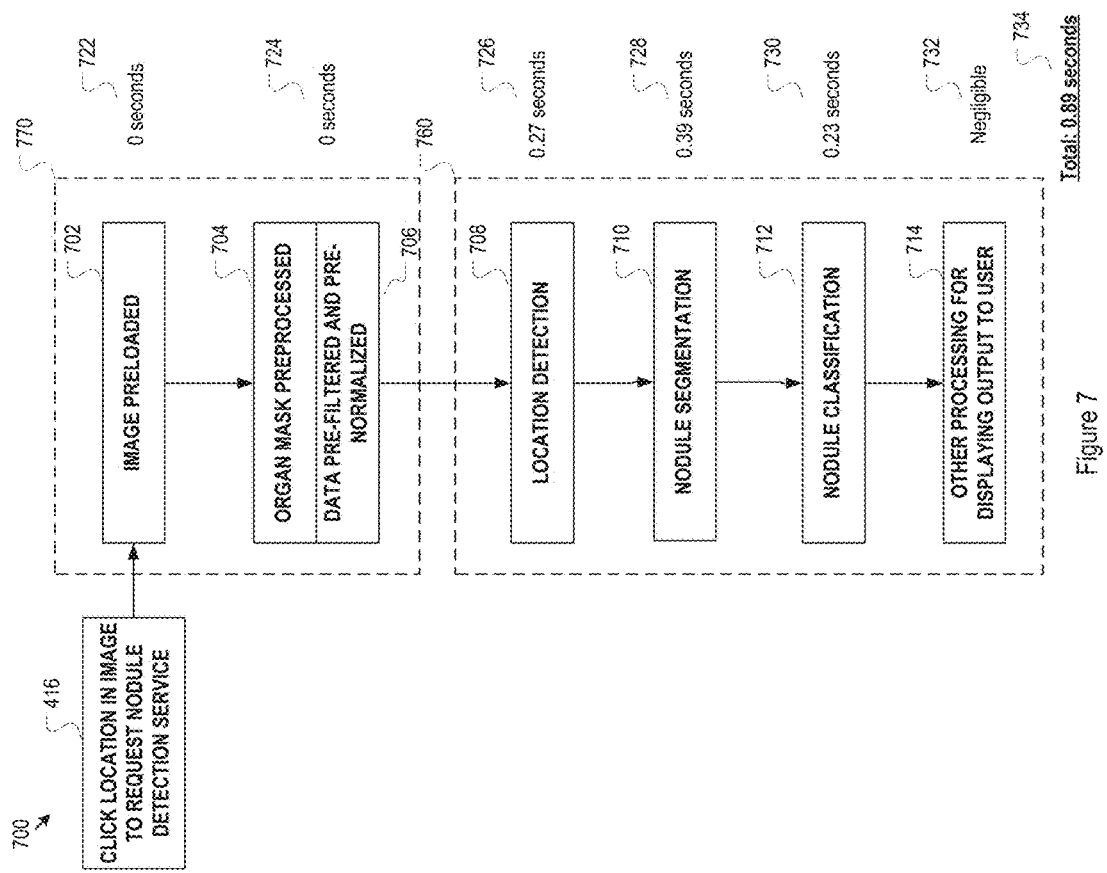
FIG. 7 illustrates improvement in response time to a request for identifying and analyzing nodules in a medical image using a data analytics pipeline with predictive pre-configuration and pre-processing.

FIGS. 6 and 7 shows an example comparison of response time between an actual request for nodule detection service and the time when the service is complete with and without predictive pre-configuration and pre-processing. As shown in FIG. 6, without pre-configuration and pre-processing, the various data analytics and processing components are largely processed in serial (load image 602→organ mask generation 604→data filtering and normalization 606→click location detection 608→nodule segmentation→610→nodule classification 612→other output processing). In the example of FIG. 6, the entire data analytics process takes 7.6 second to complete (with time break down listed in FIG. 6). In other words, from the time the radiologist clicks a suspicious location in the medical image being inspected, it would take almost 8 seconds for the radiologist to receive the output nodule segmentation and classification. In comparison, predictive pre-configuration and pre-processing completely eliminate time lags for some data analytics components shown in FIG. 6 or significant reduce the processing time for some other data analytics components due to, for example, pre-configuration and pre-loading of deep learning models. The response time improvement is shown in FIG. 7 (FIG. 7 is otherwise identically indexed as FIG. 6, except that the indexes begins with digit "7" rather than "6"). FIG. 7 shows that the total response time perceived by the radiologist is reduced to 0.89 second due to the predictive pre-configuration and pre-processing.

Figure 8:
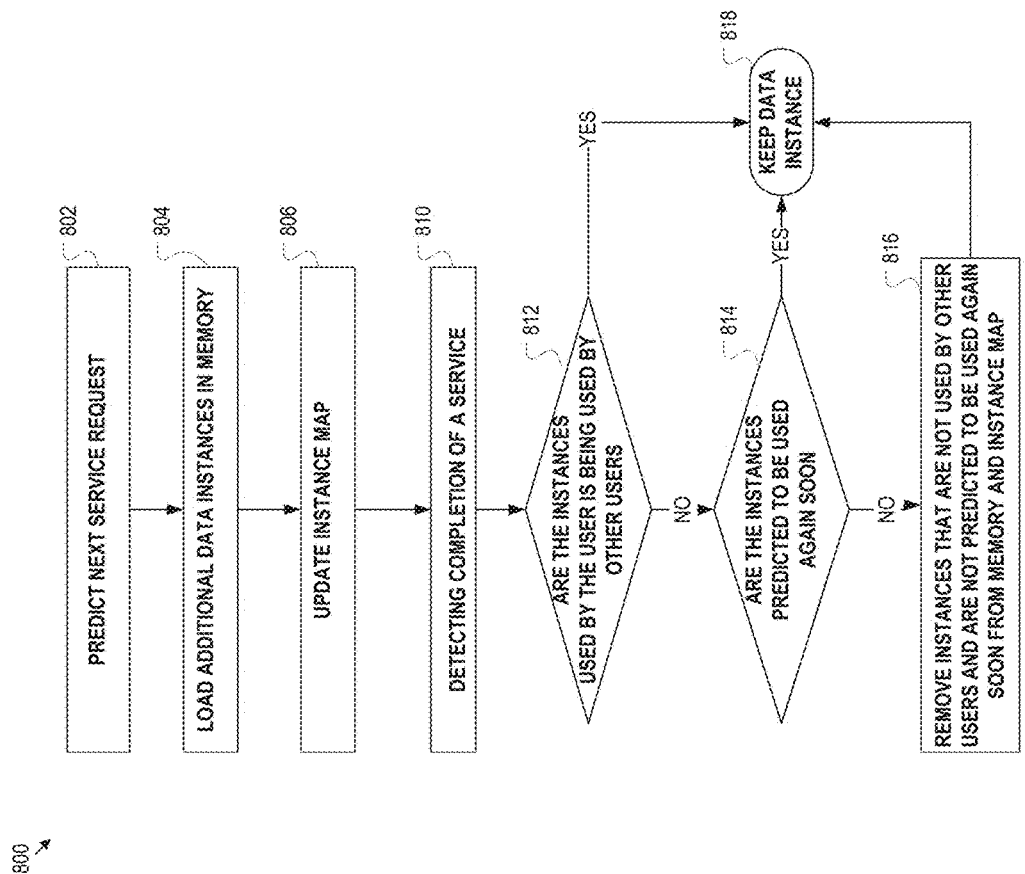
FIG. 8 illustrates an example logic flow for instantiation and decommission of cached data instances for providing real-time response to requests for detached data analytics services.

FIG. 8 further illustrates an example logic flow for managing in-memory instances of target dataset and intermediate data items generated by the data analytics components described above. The implementation illustrated in FIG. 8 is capable of efficiently handling the instantiation and decommission of data instances that may be shared by different remote users (remote terminals) and/or different data analytics services. The association between the active in-memory data instances, the users/user terminals, and the data analytics services are tracked in a data instance map that may be managed by the RPIS and data analytics servers. In step 802, the RPIS predicts the next service request by one of a plurality of users (user terminals). In step 804, target dataset or other relevant existing data for the predicted service may be loaded into the memory if they do not correspond to an active entry in the data instance map already. In step 806, the data instance map is updated to include an entry for each loaded data. Each newly created entry in the data instance map may include an association between the data instance and the identity of the user (or user terminal) invoking the data instance, and the corresponding data analytics service. In step 810, The RPIS or data analytics servers determine that a service using a particular in-memory data instance is completed. In step 812, the RPIS or data analytics servers determine whether that particular data instance is still actively associated with other users or services. If the data instance is being actively used by other users and services, the data instance will be maintained in the memory (818), and only the association between the data instance and the completed service is removed from the data instance map. If the data instance is currently inactive, the RPIS or data analytics servers may further determine, in step 814, whether the data instance is likely to be invoked again in the near future, based on, for example, current and historical user interaction operations. If it is determined that the data instance is likely to be used again in the new future, the data instance is kept in the memory without being decommissioned or removed (818). However, the RPIS or data analytics servers may request removal of the data instance from the memory and removal of entries associated with the data instance in the data instance map if it is determined that the data instance is inactive and is unlikely to be used again in the near future (816). By managing the data instances and data instance map in a multi-user and multi-service environment in the manner described in FIG. 8, status of shared data instances may be tracked and used for their instantiation and decommission in the memory.

Figure 9:
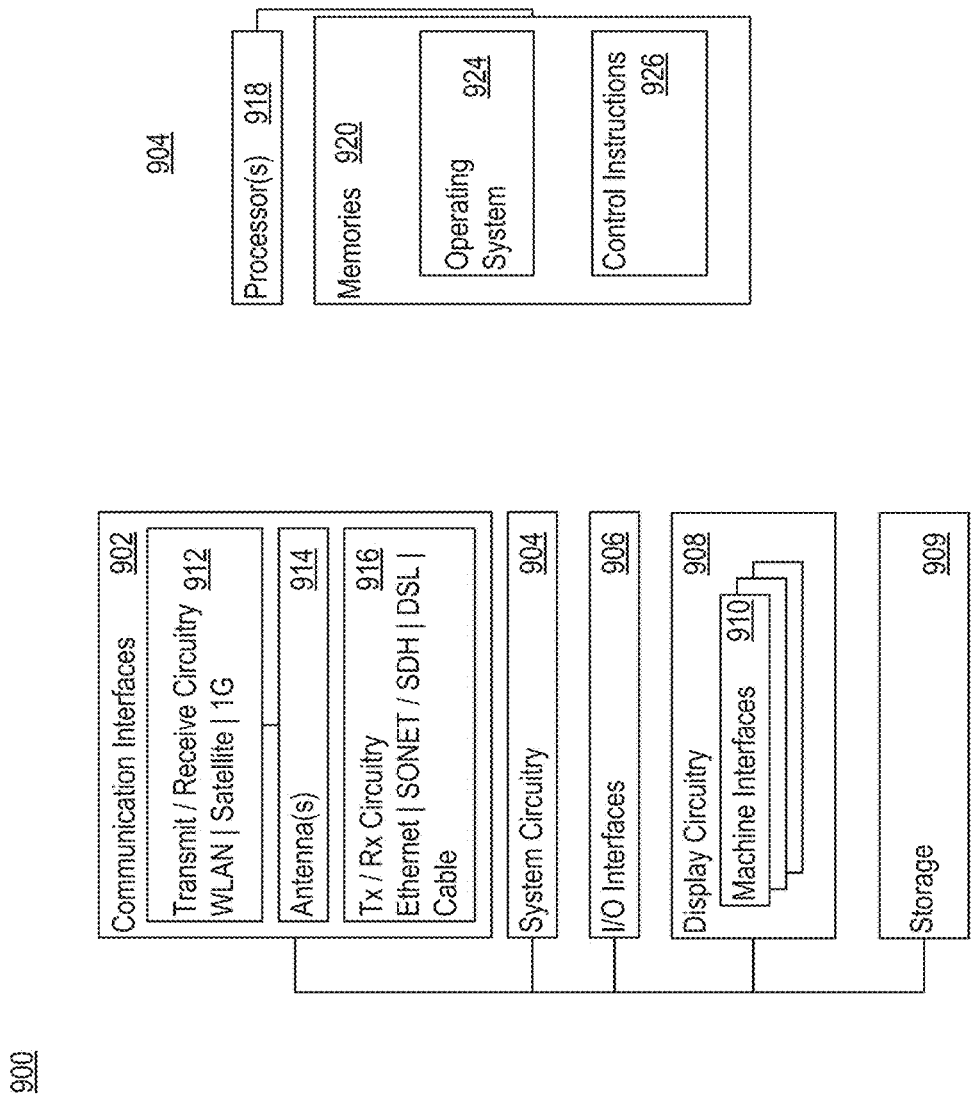
FIG. 9 illustrates a computer system that may be employed as a remote terminal or data analytics server in the system of FIGS. 1 and 2.

Finally, FIG. 9 shows an exemplary computer system 900 for implementing any of the terminal or server computing components above. The computer system 900 may include communication interfaces 902, system circuitry 904, input/output (I/O) interfaces 906, storage 909, and display circuitry 908 that generates machine interfaces 910 locally or for remote display, e.g., in a web browser running on a local or remote machine. The machine interfaces 910 and the I/O interfaces 906 may include GUIs, touch sensitive displays, voice or facial recognition inputs, buttons, switches, speakers and other user interface elements. Additional examples of the I/O interfaces 906 include microphones, video and still image cameras, headset and microphone input/output jacks, Universal Serial Bus (USB) connectors, memory card slots, and other types of inputs. The I/O interfaces 906 may further include magnetic or optical media interfaces (e.g., a CDROM or DVD drive), serial and parallel bus interfaces, and keyboard and mouse interfaces.

The communication interfaces 902 may include wireless transmitters and receivers ("transceivers") 912 and any antennas 914 used by the transmitting and receiving circuitry of the transceivers 912. The transceivers 912 and antennas 914 may support Wi-Fi network communications, for instance, under any version of IEEE 802.11, e.g., 802.11n or 802.11ac. The communication interfaces 902 may also include wireline transceivers 916. The wireline transceivers 916 may provide physical layer interfaces for any of a wide range of communication protocols, such as any type of Ethernet, data over cable service interface specification (DOCSIS), digital subscriber line (DSL), Synchronous Optical Network (SONET), or other protocol.

The storage 909 may be used to store various initial, intermediate, or final data. The storage 909 may be separate or integrated with the one or more repositories 140 and 150 of FIG. 1. The storage 909 may be centralized or distributed, and may be local or remote to the computer system 900. For example, the storage 909 may be hosted remotely by a cloud computing service provider.

The system circuitry 904 may include hardware, software, firmware, or other circuitry in any combination. The system circuitry 904 may be implemented, for example, with one or more systems on a chip (SoC), application specific integrated circuits (ASIC), microprocessors, discrete analog and digital circuits, and other circuitry. The system circuitry 904 is part of the implementation of any desired functionality related to the system 100 of FIG. 1. As just one example, the system circuitry 904 may include one or more instruction processors 918 and memories 920. The memories 920 stores, for example, control instructions 926 and an operating system 924. In one implementation, the instruction processors 918 executes the control instructions 926 and the operating system 924 to carry out any desired functionality related to any of the terminal and server components of FIG. 1.

The methods, devices, processing, and logic described above may be implemented in many different ways and in many different combinations of hardware and software. For example, all or parts of the implementations may be circuitry that includes an instruction processor, such as a Central Processing Unit (CPU), microcontroller, or a microprocessor; an Application Specific Integrated Circuit (ASIC), Programmable Logic Device (PLD), or Field Programmable Gate Array (FPGA); or circuitry that includes discrete logic or other circuit components, including analog circuit components, digital circuit components or both; or any combination thereof. The circuitry may include discrete interconnected hardware components and/or may be combined on a single integrated circuit die, distributed among multiple integrated circuit dies, or implemented in a Multiple Chip Module (MCM) of multiple integrated circuit dies in a common package, as examples.

The circuitry may further include or access instructions for execution by the circuitry. The instructions may be stored in a tangible storage medium that is other than a transitory signal, such as a flash memory, a Random Access Memory (RAM), a Read Only Memory (ROM), an Erasable Programmable Read Only Memory (EPROM); or on a magnetic or optical disc, such as a Compact Disc Read Only Memory (CDROM), Hard Disk Drive (HDD), or other magnetic or optical disk; or in or on another machine-readable medium. A product, such as a computer program product, may include a storage medium and instructions stored in or on the medium, and the instructions when executed by the circuitry in a device may cause the device to implement any of the processing described above or illustrated in the drawings.

The implementations may be distributed as circuitry among multiple system components, such as among multiple processors and memories, optionally including multiple distributed processing systems. Parameters, databases, and other data structures may be separately stored and managed, may be incorporated into a single memory or database, may be logically and physically organized in many different ways, and may be implemented in many different ways, including as data structures such as linked lists, hash tables, arrays, records, objects, or implicit storage mechanisms. Programs may be parts (e.g., subroutines) of a single program, separate programs, distributed across several memories and processors, or implemented in many different ways, such as in a library, such as a shared library (e.g., a Dynamic Link Library (DLL)). The DLL, for example, may store instructions that perform any of the processing described above or illustrated in the drawings, when executed by the circuitry.

From the foregoing, it can be seen that this disclosure provides a system and a method for providing enhanced real-time or near-real-time response to requests for detached data analytics services. For example, a system and a method are disclosed for automatically and intelligently predicting a data analytics service that may be requested by a user based on real-time user interactive operations, and for pre-loading/pre-configuring a pipeline of data analytics components to perform the data analytics service before an actual request is made by the user. Additionally, at least some intermediate data may be calculated by the pre-configured pipeline and may be cached in memory for speedy access prior to the actual user request. Upon actual user request for the data analytics service, the data analytics service would have loaded and preconfigured the data analytics pipeline, calculated and cached intermediate data, and would only need to complete a portion of the data analytics that require additional input data that are provided in real-time with the request. In such a manner, user-perceived delay in completing the detached data analytics service after the service request is made may be greatly reduced.

What is claimed is:

1. A system for providing data analytics services, comprising:
a cache memory for storing preprocessed intermediate data instances; and
a circuitry in communication with the cache memory and configured to:
monitor user interactive operations on a first remote terminal;
automatically predict, based on the interactive operations, a data analytics service that the first remote terminal is likely to request next among a predetermined plurality of data analytics services;
prior to receiving a request from the first remote terminal for the data analytics service, automatically:
identify a target data item for the data analytics service based on the interactive operations,
determine a pipeline of data analytics models associated with the data analytics service and corresponding model parameters,
instantiate the pipeline of data analytics models from a model repository and pre-configure the data analytics models with the corresponding model parameters, and
pre-process the target data item using a first portion of the instantiated and pre-configured pipeline of data analytics models into an intermediate data item and store the intermediate data item as an intermediate data instance in the cache memory; and
upon receiving from the first remote terminal the request to perform the data analytics service, process the cached intermediate data instance by a second portion of the instantiated and pre-configured pipeline of data analytics models according to at least one additional processing parameter in the request to perform the data analytics service.

2. The system of claim 1, wherein the circuitry is further configured to determine whether to remove the intermediate data instance from the cache memory after completion of the requested data analytics service based on monitoring additional user interactive operations from the first remote terminal.

3. The system of claim 2, wherein the circuitry is configured to remove the intermediate data instance from the cache memory after completion of the requested data analytics service and after determining that the additional user interactive operations from the first remote terminal indicate that a user of the first remote terminal has stopped operating on the target data item for a predetermined period of time.

4. The system of claim 1, wherein:
the circuitry is further configured to monitor interactive operations and requests for data analytics services from at least one second remote terminal; and
the cache memory is further configured to store a data instance map for associating each of the pre-processed intermediate data instances with one or more remote terminals among the first remote terminal and the at least one second remote terminal.

5. The system of claim 4, wherein the circuitry is further configured to determine whether to remove an association between the intermediate data instance generated by the first portion of the pipeline of data analytics models and the first remote terminal from the data instance map after completion of the requested data analytics service, based on monitoring additional user interactive operations from the first remote terminal.

6. The system of claim 5, wherein the circuitry is further configured to identify an inactive intermediate data instance and remove the inactive intermediate data instance from the cache memory.

7. The system of claim 6, wherein the circuitry is configured to identify the inactive intermediate data instance by determining that a corresponding intermediate data instance has no association with any of the first remote terminal and the at least one second remote terminal.

8. The system of claim 1, wherein:
the target data item comprises a medical image; and
the target data item is displayed in an interactive user interface of the first remote terminal.

9. The system of claim 8, wherein the circuitry is configured to automatically predict the data analytics service by performing predictive analytics of user interactive operations on the target data item displayed on the interactive user interface of the first remote terminal using deterministic or stochastic models based on the user's workflow.

10. The system of claim 8, wherein the data analytics service comprises a nodule detection service for identifying a nodule in the medical image.

11. The system of claim 10, wherein the pipeline of data analytics models comprises an image segmentation model for generating a mask for a predetermined organ in the medical image and a nodule segmentation model for identifying a nodule in the medical image.

12. The system of claim 11, wherein the image segmentation model and the nodule segmentation model each comprises a plurality of convolutional neural network layers.

13. The system of claim 11, wherein:
the first portion of the instantiated and pre-configured pipeline of data analytics models comprises the image segmentation model;
the second portion of the pipeline of data analytics models comprises the nodule segmentation model; and
the intermediate data instance generated by the first portion of the pipeline of data analytics models comprises the medical image filtered by the mask for the predetermined organ.

14. The system of claim 13, wherein:
the additional processing parameter in the request to perform the data analytics service from the first remote terminal comprises a user-selected location in the image displayed on the interactive user interface of the first remote terminal as indicated by a cursor click operation by a user initiating the request; and
the circuitry is configured to process the cached intermediate data instance by the nodule segmentation model according to the user-selected location to determine a mask for a nodule in a vicinity of the user selected location in the medical image.

15. The system of claim 11, wherein
the pipeline of data analytics models further comprises a data normalization model for normalizing the medical image filtered by the mask;
the first portion of the pipeline of data analytics models comprises the image segmentation model and the data normalization model;
the second portion of the pipeline of data analytics models comprises the nodule segmentation model; and
the intermediate data instance comprises the medical image filtered by the mask and filtered by the data normalization model.

16. The system of claim 15, wherein the pipeline of data analytics models further comprises a malignancy detection model for predicting whether the nodule identified by the nodule segmentation model is malignant.

17. The system of claim 15, wherein
the additional processing parameter in the request to perform the data analytics service from the first remote terminal comprises a user-selected location in the image displayed on the interactive user interface of the first remote terminal as indicated by a cursor click operation by a user initiating the request; and
the circuitry is configured to process the cached intermediate data instance by the nodule segmentation model according to the user-selected location to determine a mask for a nodule in a vicinity of the user selected location in the medical image.

18. A method for providing data analytics services by a system circuitry, comprising:
monitoring user interactive operations on a first remote terminal;
automatically predicting, based on the interactive operations, a data analytics service that the first remote terminal is likely to request next among a predetermined plurality of data analytics services;
prior to receiving a request from the first remote terminal for the data analytics service, automatically:
identifying a target data item for the data analytics service based on the interactive operations,
determining a pipeline of data analytics models associated with the data analytics service and corresponding model parameters,
instantiating the pipeline of data analytics models from a model repository and preconfigure the data analytics models with the corresponding model parameters, and
pre-processing the target data item using a first portion of the instantiated and pre-configured pipeline of data analytics models into an intermediate data item and store the intermediate data item as an intermediate data instance in the cache memory; and
upon receiving from the first remote terminal the request to perform the data analytics service, processing the cached intermediate data instance by a second portion of the instantiated and pre-configured pipeline of data analytics models according to at least one additional processing parameter in the request to perform the data analytics service.

19. The method of claim 18, further comprising removing the intermediate data instance from the cache memory after completion of the requested data analytics service and after determining that additional user interactive operations from the first remote terminal indicate that a user of the first remote terminal has stopped operating on the target data item for a predetermined period of time.

20. The method of claim 18, wherein:
the target data item comprises a medical image;
the target data item is displayed in an interactive user interface of the first remote terminal;
the data analytics service comprises a nodule detection service for identifying a nodule in the medical image;
the first portion of the pipeline of data analytics models comprises an image segmentation model for generating a mask for a predetermined organ in the medical image;

the second portion of the pipeline of data analytics models comprises a nodule segmentation model for identifying a nodule in the medical image; and the intermediate data instance processed by the first portion of the pipeline of data analytics models comprises the medical image filtered by the mask for the predetermined organ.

\* \* \* \* \*